United States Patent [19]

Pevere

[11] Patent Number: 5,610,275
[45] Date of Patent: Mar. 11, 1997

[54] REAGENT USEFUL FOR CLEAVING AND PROCESS FOR USING THIS REAGENT

[75] Inventor: Virginie Pevere, Lyons, France

[73] Assignee: Rhone-Poulenc Chimie, Courbevoie, France

[21] Appl. No.: 332,434

[22] Filed: Oct. 31, 1994

Related U.S. Application Data

[63] Continuation of Ser. No. 958,258, Oct. 9, 1992, abandoned.

[30] Foreign Application Priority Data

Oct. 11, 1991 [FR] France .................................. 91 12524

[51] Int. Cl.$^6$ .............................. A61K 38/00; C07K 1/00
[52] U.S. Cl. ............................................. 530/338; 568/716
[58] Field of Search ............................... 530/338; 568/716

[56] References Cited

FOREIGN PATENT DOCUMENTS

| 1182450 | 2/1970 | European Pat. Off. . |
| 0432022 | 6/1991 | European Pat. Off. . |

OTHER PUBLICATIONS

A Cleavage Method Which Minimizes Side Reactions Following Fmoc Solid Phase Peptide Syntheses, King et al., International Journal of Peptide and Protein Research, 36:255–266 (1990).

Chlorotrimethylsilane–Phenol as a Mild Deprotection Reagent for the Tert–Butyl Based Protecting Groups in Peptide Synthesis, Kaiser et al., Tetrahedron Letters, 29(3):303–306 (1988).

Improved Selectivity in the Removal of the Tert–Butyloxycarbonyl Group, Bodanszky et al., Chemical Abstracts, 101:171728b (1984).

Deprotection of Carboxylic Esters of β–Lactam Homologues. Cleavage of p–Methoxybenzyl, Diphenylmethyl, and Tert–Butyl Esters Effected by a Phenolic Matrix, Torii et al., Journal of Organic Chemistry, 56:3633–3637 (1991).

Ueki et al. Bull. Chem. Soc. Japan vol. 44, 1108–1111 (1971).

King et al. Int. J. Pept. Prot. Res. vol. 36 (1990) 255–266.

Torii et al. J. Org. Chem. (1991) pp. 3633–3637.

Kaiser et al. Tet. Lett. vol. 29 pp. 303–306 (1988).

Bodanszky et al. CA 101: 171728b (1984).

Stewart & Young, *Solid Phase Peptide Syntheses* (2nd ed.) (Pierce 1984) p. 5.

*Primary Examiner*—Michael P. Woodward
*Assistant Examiner*—Benet Prickril
*Attorney, Agent, or Firm*—Finnegan, Henderson, Farabow, Garrett & Dunner, L.L.P.

[57] ABSTRACT

The invention relates to a reagent which is useful for cleaving an alkoxycarbonyl group from a functional group which it is protecting and to a process for using this reagent. This reagent comprises a phenol, a diluent, and a hydrohalic or hydropseudohalic acid, the acidity of which is at least equal to that of formic acid. The method is advantageously applied in the synthesis of peptides.

9 Claims, No Drawings

REAGENT USEFUL FOR CLEAVING AND PROCESS FOR USING THIS REAGENT

This application is a continuation, of application Ser. No. 07/958,258 filed Oct. 9, 1992, now abandoned.

TECHNICAL FIELD OF INVENTION

The subject of the present invention is a reagent and a process for using the reagent to cleave an alkoxycarbonyl protecting group from a functional group that it protects during an organic synthesis.

BACKGROUND OF THE INVENTION

It is a known procedure to protect a molecule during a chemical synthesis by blocking, with appropriate protecting groups, functional groups which would otherwise be reactive, but which are not intended to react during the synthesis procedure being carried out. These protecting groups are then removed following the synthesis procedure.

This technique is particularly useful during peptide syntheses. The most commonly protected functional groups are amine, alcohol or thiol functional groups. The most commonly used protecting groups include the tert-butyloxycarbonyl group (BOC), the benzyloxycarbonyl group (Z) or, indeed, even the fluorenylmethoxycarbonyl group (FMOC).

The deprotection technique conventionally used is a lysis in acidic medium, generally in anhydrous hydrohalic medium (that is to say, with a water content which is generally less than 1%, advantageously less than $10^{-3}\%$, and preferably less than $10^{-4}\%$.

However, this technique has many disadvantages. The cleaving (deprotection) reaction is sometimes slow or requires a large excess of reagent. The alkoxy groups that result have a tendency to be converted into carbocations, leading to formation of double bonds where possible, or alkylation reactions on the nucleus, which is a particular nuisance in the case of peptide syntheses in which the sequence has nucleophilic residues, such as aromatic nuclei (tryptophan, tyrosine, phenylalanine, or the like) or sulphur-containing residues (methionine).

SUMMARY OF THE INVENTION

Consequently, one of the objects of the present invention is to provide a process and a reagent which substantially accelerate the kinetics of the deprotection reaction.

Another object of the present invention is to provide a reagent and a process which favor the formation of halide or of pseudohalide cleavage products as opposed to the formation of unsaturated product(s).

Another object of the present invention is to provide a process and a reagent which prevent alkylation reactions on the aromatic nuclei.

More generally, one of the objects of the present invention is to provide a process which makes it possible to trap species of the carbocation type, leading to halide or pseudohalide cleavage products.

Throughout this description and the claims that follow, the term "reagent" is used to describe a hereinafter specified combination of chemical materials.

DESCRIPTION OF THE PREFERRED EMBODIMENTS

The above stated objects and others are achieved by means of a reagent which is useful especially for cleaving an alkoxycarbonyl group from the functional group that it protects, which reagent comprises a phenol B;

a diluent A; and an anhydrous hydrohalic or pseudohydrohalic acid, the acidity of which, expressed by the Hammett constant, is at least equal to that of formic acid, and preferably, at least equal to that of hydrochloric acid.

It will be understood that the expression phenol B refers to a phenol or mixtures of phenols.

The water content of the hydrohalic or pseudohydrohalic acid is advantageously as low as possible, preferably no more than about 3% by weight based on the acid, and more preferably no greater than the values mentioned above, i.e., less than about 1%, and most preferably less than about $10^{-3}$ or $10^{-4}\%$.

The acid content of the anhydrous hydrohalic or hydropseudohalic acid is generally, and especially for the preferred acids, limited by the solubility of the acid in the medium (i.e., the phenol-diluent mixture). When solubility in the medium is not so limited, the acid content should not exceed 10% by weight of the sum of diluent A and phenol B.

The quantity of phenol B is preferably at least 1/200 of diluent A. There is no precise upper limit of the ratio of phenol B to diluent A. In fact, phenol B (pure product or mixture) can be used without diluent A if the following conditions are fulfilled:

the melting point of phenol B is equal to or less than 50° C.;

phenol B can be separated from the reaction product by distillation, optionally under reduced pressure;

phenol B is not water-miscible in all proportions; preferably, it dissolves no more than about 10% by weight, more preferably, about 5%, and most preferably about 1%, of water;

it is also preferable that the water be only able to dissolve at most about 10% of phenol B, preferably at most about 1%, by weight, even in the presence of diluent A as a third solvent; and phenol B does not form a stable emulsion capable of interfering with the removal of the by-products by washing with water.

The halophenols, particularly di-, and preferably monochlorophenols, and the lower alkyl alkylphenols, for example, correspond to these constraints.

It is, however, preferable that there be both a diluent A and a phenol B in the reagent. The weight ratio of the phenol B to the diluent A is about 1/200 to 1, preferably about 1/20 to 1/2.

The values expressed above as mass ratios are well-suited for phenol per se ($C_6H_5OH$) and for phenols whose molecular mass is not significantly different from that of phenol. For the phenols with high molecular weights, the concentration of phenol in mole per liter of water is at least equal to about $5\times10^{-2}$, preferably from 0.1 to 2, and most preferably from 0.5 to 1.5 M. When diluent A and phenol B are not miscible in all proportions, the upper limit of the phenol content is the lower of the weight limit mentioned above and the solubility limit.

Diluent A is an organic solvent which is sufficiently polar to dissolve at least 1%, preferably at least 2%, by weight of phenol per se and is sufficiently hydrephobic as not to be miscible with water in all proportions.

It is preferable that the water dissolve not more than 10%, preferably not more than 5%, and most preferably not more than 1% by weight of diluent A, even in the presence of phenol B as a third solvent.

Diluent A preferably has a low basicity, that is to say, its donor index (or nucleophilicity index as defined by Reichardt C., *Solvent Effect in Organic Chemistry*, Verlag Chemie, Weinheim, N.Y. 1979; Reichardt C. and Harbusch-Gornert E., *Justus Liebigs Ann. Chem.* 721 (1983)) is at most equal to and preferably less than approximately that of tetrahydrofuran. The donor index is in principle less than the enthalpy value, expressed in kcal/mole, of the interaction between the solvent and antimony in dilute methylene chloride solution (cf. V. Gutmann, *Electrochim. Acta* 21:661 (1976); V. Gutmann and E. Wychera, *Inorg. Nucl. Chem. Lett.* 2:297 (1966); V. Mayer and V. Gutmann, *Monatsh. Chem.* 101:912 (1970)).

The diluents must not be protic acids as their pKa must for best results be not less than about 15, preferably not less than about 20, and more preferably not less than about 30.

Diluent A can be a mixture, including petroleum fractions. Naturally, diluent A must be inert, under the operating conditions, with respect to the phenols and peptide synthesis reagents used. The preferred families of diluents are chosen from the group consisting of aromatic compounds, ethers, esters and halogenated solvents. Examples of members of these families, include, as halogenated aliphatic compounds; dichloromethane, 1,2-dichloroethane or 1,1,1-trichloroethane; as aromatic compounds; toluene; and as halogenated aromatic compounds; chlorobenzene; as esters, ethyl acetate and isopropyl acetate; and as ethers, tertbutyl methyl ether and anisole.

For reasons of industrial economics, it is preferable that diluent A be distillable at atmospheric pressure or under primary or secondary vacuum.

In general, phenol B is chosen from the group of compounds corresponding to the following formula I.

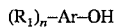
$$(R_1)_n-Ar-OH \qquad (I)$$

in which:

Ar represents a heterocyclic or homocylic, monocyclic or polycyclic, aromatic radical;

the substituents $R_1$, which are the same or different, represent:

a halogen, preferably fluorine, chlorine or bromine, a group $-Z-R_2$, where Z can be
a single bond,
an oxygen atom, and
$R_2$ represents a hydrogen atom or an optionally hydroxylated or mono- or polyhalogenated alkyl or aryl radical containing at most 8 carbon atoms; and n represents the number of substituents $R_1$ on Ar and is equal to 0 or to an integer at most equal to the number of positions which can be substituted on the aromatic nuclei. As stated above, phenol B can be one or a mixture of compounds of formula I.

The alkyl groups (as defined in the *Dictionnaire de la Chimie Duval*, Presse Scientifique Internationale, Paris VIe, 1959) can be, in particular, linear or branched aliphatic residues containing at most six carbon atoms or arylaliphatic residues.

The number of positions which can be substituted can be easily determined using simple rules known to those skilled in the art.

Thus, for example:

when Ar=phenyl, n<5

Ar=naphthyl, n<7.

Preferably, the number of carbon atoms of phenol B is at most 30 carbon atoms, preferably at most 20 carbon atoms.

Preferably, the phenol is not basic, that is to say, when there is a hetero atom in the ring, the said hetero atom is not chosen from column VB of the Periodic Classification of the Elements (cf. Bull. Soc. Chim. No. 1 Suppl., January 1966).

It is desirable that the positions vicinal to the phenol functional group be unsubstituted or occupied by groups which are not sterically hindering. Those considered as sterically hindering are radicals connected to the said vicinal positions by a tertiary, or even secondary, carbon.

The monocyclic compounds provide the best compromise between efficiency and cost; those containing six members (pyridyl or phenyl) are preferred.

It is also desirable that $Z-R_2$ not denote more than three hydroxyl groups and preferably not more than 2.

Preferably, in the formula I, the radicals R are chosen from the group consisting of:

methyl, ethyl, propyl and butyl radicals, trifluoromethyl and pentafluoroethyl radicals, methoxy, ethoxy, propoxy and butoxy radicals, phenyl, hydroxyphenyl, and Ar-OH radicals, phenoxy and hydroxyphenoxy radicals, and fluorine, chlorine and bromine atoms.

In order not to make the phenol molecule too heavy, it is desirable that, in the formula I, n be at most equal to 5.

The phenols that give the best results include:

monohalophenols (preferably monochloro), polyhalophenols (preferably polyfluoro), phenols that are mono- or disubstituted by $C_1$–$C_4$ alkyl, $C_1$–$C_4$ alkoxy, $C_1$–$C_2$ perfluoroalkyl and 2,2,2-trifluoroethyl radicals, diphenols, phenol per se (i.e., $C_6H_5OH$); and naphthols, optionally mono- or disubstituted.

It is preferable that the quantity of phenol be at least equal to that which corresponds to one mole of phenol per amino acid unit and advantageously one mole to three amino acid units.

The amino acid can be C- or N-protected; in the latter case, the acid group can be activated on the acid functional group, with the acid side groups protected, and the amino acids can be natural or synthetic.

For a further discussion of the solvent medium, see U.S. patent application No. 07/621,468, which is incorporated in its entirety herein. The medium according to the present invention also makes it possible to dissolve a protected peptide.

The preferred hydrohalic acid is chosen from hydrobromic, hydriodic, and preferably hydrochloric acid and their mixtures. It is also possible to employ acids corresponding to pseudohalogens, such as trifluoromethanesulphonic (triflic) acid. The alkoxycarbonyl groups can be written in the form of R-O-CO- where R represents an alkyl group including aralkyl, alkyl having the definition given in the *Dictionnaire de la Chimie Duval*, Presse Scientifique Internationale, Paris VIe, 1959.

The alkyl group preferably represents an alkyl group having at most 15 carbon atoms and preferably at most 7 carbon atoms. The group R is preferably a secondary, and for best results a tertiary group, such as the tert-butyl group, which is one of the preferred radicals. The radical can also be an aralkyl group which contains at most 10 nuclei and preferably from 1 to 8 nuclei. There may be mentioned, in particular, the benzyl group, the FMOC group or the groups described in British Patent Application No. 90/28208.8 filed Dec. 31, 1990.

The concentration of hydrohalic acid is advantageously maintained at a value at least equal to the solubility of the gas in the medium at equilibrium with a partial pressure at least equal to $10^3$ preferably equal to $10^4$ pascals and in general equal to that obtained by sparging the said hydrohalic acid at atmospheric pressure. It is also possible to carry out the procedure at a higher pressure.

Insofar as it is possible to show a range, it is desirable that the concentration of acid, and thus the solubility expressed in mole(s) per liter, is at least equal to $10^{-4}$ M and preferably from $10^{-3}$ to $10^{-1}$ M.

The temperature does not need to be very high. For example, the temperature can be between the temperature at which the mixture begins to melt and approximately 100° C., or at the boiling temperature of the reaction system when this temperature is less than 100° C.

The technique of this invention is particularly well-suited to the synthesis of peptides, especially oligopeptides containing about 2 to 50, and preferably from 5 to 25, amino acids.

In a general way, the solvent system makes it possible for the carbocation(s) generated by the reaction of hydro- or pseudohydrohalic acid with a substrate or a reagent, namely $R^+$, to develop towards a halide or pseudohalide form. Thus, the reagent is also useful for the synthesis of (pseudo)halides from compounds which make carbocation (corresponding to the desired halides) generation possible in an anhydrous acidic medium. The inventor theorizes that the reaction takes place via an intermediate phenol ether (not very stable under the operating conditions but present at significant levels during the reaction). Thus, the present reagent can be useful for synthesizing mixed ethers of phenols with the radical R; among the phenols that can be used are penta-substituted phenols, such as the pentahalophenols (with the same preferences for the halogens as those mentioned above), so as to avoid any degradation of the phenol by reaction of the carbocation with the latter.

The following examples which illustrate the invention are non-limiting as it is understood that one skilled in the art will have the capability to use the teachings of the present invention in other applications.

EXAMPLES

GENERAL PROCEDURE

A protected oligopeptide is dissolved in a mixture of methylene chloride and an aromatic hydroxyl compound. This reaction mixture is subjected to sparging with gaseous hydrochloric acid until the existence of the protected oligopeptide can no longer be detected.

Example 1

The reaction was carried out on the oligopeptide BOCPheLeu OPGC in methylene chloride a) in the presence of phenol ($C_6H_5OH$), b) in the presence of orthocresol, and c) with no phenolic compound at all. OPGC is a benzyl-type O-protecting group. Deprotection was accomplished at room temperature by sparging with HCl (flow rate 1 l/h). The results are presented in the following Table:

| % Ar—OH in $CH_2Cl_2$ | Cleaving time |
|---|---|
| Zero | 60 min |
| Phe—OH 10% | 30 min |
| $CH_3$—Phe—OH 10% | 30 min |

Example 2

Deprotection in the presence of phenol (or orthocresol)

The solubility of HCl in $CH_2Cl_2$ was explored as a possible explanation of the observed acceleration of cleaving time in Example 1. Ten percent phenol in $CH_2Cl_2$ was sparged for 40 min with HCl and the acidity of the mixture was determined twice:

1st determination: 0.06 M HCl in the solvent;

2nd determination: 0.03 M HCl in the solvent.

It was thus demonstrated that HCl has very little solubility in a $CH_2Cl_2$/ArOH (10%) mixture and therefore, the acceleration in the reaction rate cannot be explained by a very large solubilization of HCl in $CH_2Cl_2$. It is theorized that the accelerated reaction rate may be due to the presence of an intermediate. During the deprotection step, the presence of the intermediate Ar-O-C($CH_3$)$_3$ was detected. This material did not accumulate in the reaction mixture: it was itself cleaved by HCl. This reaction appeared to be rapid:

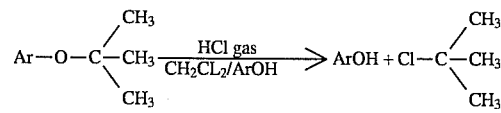

Other phenols such a pentafluorophenol also gave good results.

It will be apparent to those skilled in the art that various modifications and variations can be made in the reagent and process of the present invention. Thus, it is intended that the present invention cover modifications and variations of this invention which fall within the scope of the appended claims and their equivalents.

What is claimed is:

1. An anhydrous reagent useful for cleaving an alkoxycarbonyl protecting group from a functional group that it protects, which reagent consists essentially of
   a) a phenol having the general formula $(R_1)_n$-Ar-OH wherein Ar represents a phenyl ring, $R_1$ represents a halogen atom or a group -Z-$R_2$, where Z can be a single bond connecting $R_2$ to Ar or an oxygen atom and $R_2$ represents a hydrogen atom or an optionally hydroxylated or mono- or poly-halogenated alkyl or aryl radical containing at most 8 carbon atoms; and n represents the number of substituents $R_1$ and is equal to 0 or an integer from 1 to the number of positions which can be substituted on the phenyl ring;
   b) an organic diluent that is sufficiently polar to dissolve at least 1% by weight of hydroxybenzene and sufficiently hydrophobic as to be no more than 10% by weight soluble in water; and
   c) an anhydrous hydrohalic acid, the acidity of which, expressed by its Hammett constant, is at least equal to that of formic acid.

2. A reagent according to claim 1 wherein the positions vicinal to the phenol functional group are unsubstituted or are substituted with non-sterically hindering substituents.

3. A reagent according to claim 1 wherein the diluent is chosen from aromatic compounds, ethers, esters and halogenated solvents.

4. A reagent according to claim 3 wherein the dilvent is selected from halogenated aliphatic compounds, toluene, chlorobenzene, ethyl acetate, isopropyl acetate, butyl methyl ether and anisole.

5. A reagent according to claim 4 wherein the phenol is hydroxybenzene and wherein the weight ratio of the hydroxybenzene to the diluent if about 1/200 to 1/1.

6. A reagent according to claim 1 wherein the weight ratio of the phenol to the diluent is from about 1/200 to 1/1.

7. A reagent according to claim 4 wherein the hydrohalic acid is chosen from hydrochloric, hydrobromic and hydrofluoric acids.

8. An anhydrous reagent for cleaving an alkoxycarbonyl group from a functional group that it protects, which reagent consists essentially of hydroxybenzene, a chlorinated alphatic hydrocarbon and hydrochloric acid, and the weight ratio of hydroxyenzene to chlorinated aliphatic hydrocarbon is from 1/200 to 1/1.

9. A process for cleaving an alkoxycarbonyl protecting group from a functional group that it protects, which process comprises reacting a compound containing a protected functional group with an anhydrous reagent consisting essentially of a) a phenol having the general formula $(R_1)_n$-Ar-OH wherein Ar represents a phenyl ring, $R_1$ represents a halogen atom or a group -Z-$R_2$, where Z can be a single bond connecting $R_2$ to Ar or an oxygen atom and $R_2$ represents a hydrogen atom or an optionally hydroxylated or mono- or poly-halogenated alkyl or aryl radical containing at most 8 carbon atoms; and n represents the number of substituents $R_1$ and is equal to 0 or an integer from 1 to the number of positions which can be substituted on the phenyl ring;

b) an organic diluent that is sufficiently polar to dissolve at least 1% by weight of hydroxybenzene and sufficiently hydrophobic as to be no more than 10% by weight soluble in water; and c) an anhydrous hydrohalic acid, the acidity of which, expressed by its Hammett constant, is at least equal to that of formic acid;

at a temperature between the melting point of the phenol and about 100° C.

* * * * *

UNITED STATES PATENT AND TRADEMARK OFFICE
CERTIFICATE OF CORRECTION

PATENT NO. : 5,610,275
DATED : March 11, 1997
INVENTOR(S) : Virginie PEVERE

It is certified that error appears in the above-indentified patent and that said Letters Patent is hereby corrected as shown below:

Claim 4, Col. 6, line 64, change "dilvent" to --diluent--.

Claim 5, Col. 7, line 3, change "if" to --is--.

Claim 8, Col. 7, line 13, change "hydroxyenzene" to --hydroxybenzene--.

Signed and Sealed this

Fourteenth Day of October, 1997

Attest:

BRUCE LEHMAN

Attesting Officer

Commissioner of Patents and Trademarks